(12) United States Patent
Rosevear et al.

(10) Patent No.: US 7,172,754 B1
(45) Date of Patent: *Feb. 6, 2007

(54) COSMETIC EMULSIONS WITH SUNSCREENS AND CONJUGATED LINOLEIC ACID

(75) Inventors: Jeffrey William Rosevear, Wallingford, CT (US); Marcina Siciliano, New Haven, CT (US); Brian John Dobkowski, Milford, CT (US); Bivash Ranjan Dasgupta, Hamden, CT (US); Lei Huang, Orange, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/318,417

(22) Filed: Dec. 23, 2005

(51) Int. Cl.
*A61Q 17/04* (2006.01)
*A61K 8/00* (2006.01)
*A61K 8/06* (2006.01)
*A61K 31/19* (2006.01)

(52) U.S. Cl. .................. 424/59; 424/60; 424/400; 424/401; 514/557; 514/844; 514/847; 514/937; 514/938; 514/969

(58) Field of Classification Search ............... 424/59, 424/60, 400, 401; 514/844, 847, 937, 938, 514/969, 557
See application file for complete search history.

(56) References Cited

U.S. PATENT DOCUMENTS

| | | | |
|---|---|---|---|
| 5,422,371 A | 6/1995 | Liao et al. | |
| 5,541,405 A | 7/1996 | Hassler, Jr. et al. | |
| 5,723,139 A | 3/1998 | Granger et al. | |
| 5,759,556 A | 6/1998 | Burger et al. | |
| 5,961,961 A | 10/1999 | Dobkowski et al. | |
| 6,019,990 A | 2/2000 | Remmereit | |
| 6,171,581 B1 * | 1/2001 | Joshi et al. ............... 424/65 |
| 6,287,553 B1 | 9/2001 | Alaluf et al. | |
| 6,403,064 B1 | 6/2002 | Alaluf et al. | |
| 6,524,598 B2 | 2/2003 | Sunkel et al. | |
| 6,551,602 B1 | 4/2003 | Barrett et al. | |
| 6,645,502 B2 * | 11/2003 | Sandewicz et al. .... 424/195.15 |
| 6,696,049 B2 | 2/2004 | Vatter et al. | |
| 6,953,583 B1 | 10/2005 | Ghisalberti | |
| 2003/0003068 A1 | 1/2003 | Mayes et al. | |
| 2005/0118208 A1 | 6/2005 | Bewert et al. | |
| 2005/0163730 A1 | 7/2005 | Rosevear et al. | |

FOREIGN PATENT DOCUMENTS

| | | |
|---|---|---|
| EP | 0 742 005 B1 | 4/1996 |
| EP | 0 803 247 B1 | 4/1997 |
| FR | 2 780 886 | 7/1998 |
| WO | 98/13020 | 4/1998 |
| WO | 99/26588 | 6/1999 |
| WO | 01/08650 A1 | 2/2001 |

* cited by examiner

*Primary Examiner*—Shelley A. Dodson
(74) *Attorney, Agent, or Firm*—Milton L. Honig

(57) ABSTRACT

A cosmetic water-in-oil composition is provided which includes a water-in-oil emulsifying silicone surfactant, organic sunscreen agent and conjugated linoleic acid. The conjugated linoleic acid functions to moderate shine on facial surfaces to which the organic sunscreen agent formulated composition is topically applied.

9 Claims, No Drawings

COSMETIC EMULSIONS WITH SUNSCREENS AND CONJUGATED LINOLEIC ACID

BACKGROUND OF THE INVENTION

1. Field of the Invention

The invention concerns a cosmetic emulsion composition formulated to decrease facial shine known also as gloss.

2. The Related Art

Women prefer cosmetics that impart a matte appearance. The matte finish overcomes the shiny effect engendered by greasy skin, particularly under hot and humid conditions. Absorbent fillers such as talc, silica, kaolin and other inorganic particulates have been used to achieve the effect by their optical properties.

Cosmetic formulations themselves have components which contribute to the undesirable appearance of facial shine. These are usually hydrophobic ingredients which include fatty alcohols, fatty esters and fatty acids. These components can be minimized through use of less gloss inducing hydrophobic carriers such as the silicones. Organic sunscreens contribute to the problem. Where high levels of Sun Protection Factor (SPF) are necessary, there is no ready substitute for organic sunscreens. One approach to minimizing the level of these ingredients is reported in U.S. Pat. No. 5,961,961 (Dobkowski et al.). Therein are disclosed relatively viscous lotion and cream products. A boost in SPF is achieved by use of large particle size organic sunscreen agents. This allows formulating with relatively lower levels of the organic sunscreen. There is no disclosure as to whether gloss has been reduced through these measures.

Focus of the present invention was to achieve reductions in facial gloss despite formulations which require oily components, especially organic sunscreen agents.

SUMMARY OF THE INVENTION

A cosmetic composition is provided which is a water-in-oil emulsion including:
(i) from about 0.1 to about 30% by weight of a water-in-oil emulsifying silicone surfactant;
(ii) from about 0.1 to about 30% by weight of an organic sunscreen agent; and
(iii) from about 0.1 to about 10% of a conjugated linoleic acid.

DETAILED DESCRIPTION OF THE INVENTION

Now it has been found that a water-in-oil cosmetic composition containing conjugated linoleic acid can decrease shine (gloss) when topically applied to the face. Generally, oily components including organic sunscreen agents increase shininess. It was surprising that the conjugated linoleic acids, which are oils, acted to decrease facial shine.

Conjugated Linoleic Acid

Conjugated linoleic acid (hereinafter referred to also as CLA) comprises a group of positional and geometric isomers of linoleic acid in which various configurations of cis and trans double bonds at positions (6,8), (7,9), (8,10), (9,11), (10,12) or (11,13) are possible. Thus, twenty-four different isomers of CLA exist.

The invention also includes derivatives of the free acid which thus comprise conjugated linoleic acid moieties. Preferable derivatives include those derived from substitution of the carboxyl group of the acid, such as esters (e.g. retinyl esters, triglyceride esters, monoglyceride esters, diglyceride esters, phosphoesters), amides (e.g. ceramide derivatives), salts (e.g. alkali metal and alkali earth metal salts, ammonium salts); and/or those derived from substitution of the C18 carbon chain, such as alpha hydroxy and/or beta hydroxy derivatives.

In the case of triglyceride ester derivatives, all positional isomers of CLA substituents on the glycerol backbone are included. The triglycerides must contain at least one CLA moiety. For example, of the three esterifiable positions on the glycerol backbone, the 1 and 2 positions may be esterified with CLA and by another lipid at position 3 or as an alternative, the glycerol backbone could be esterified by CLA at the 1 and 3 positions with another lipid at position 2.

Wherever the term "conjugated linoleic acid" or "CLA" is used in this specification it is to be understood that the derivatives thereof comprising CLA moieties are also included. "CLA moieties" refers to CLA fatty acyl portion(s) of a CLA derivative.

The isomers of greatest interest in the present cosmetic compositions are cis 9, trans11-linoleic acid and trans10, cis12-linoleic acid. Hereinafter the term "9,11-linoleic" or "10,12-linoleic" shall mean preferentially these two main isomers, but will include lesser amounts of the remaining isomers, particularly when obtained or derived from a natural source.

In accordance with the present invention, 9,11-linoleic acid and 10,12-linoleic acid are formulated into cosmetic preparations either as the free acid, as individual chemical derivatives, or as combinations of free acid and derivative.

By "c9, t11 and t10, c12 isomer enriched CLA" is meant that at least 30% by weight of the total CLA (and/or CLA moieties) present in the composition is in the form of the cis 9, trans 11 and trans 10, cis 12 isomers. Preferably, at least 40%, most preferably at least 50%, by weight of the total CLA and/or CLA moieties present in the composition, is in the form of the aforementioned isomers.

Amount of the CLA present in emulsions of this invention may range from about 0.1 to about 10% by weight of the composition. More preferably the amount is from about 0.5% to about 5%, and most preferably from about 1% to about 3%.

Mixed isomers of CLA are prepared by high temperature alkali treatment of Safflower oil, generating CLA with equal amounts of the c9, t11 and t10, c12 CLA isomers. CLA enriched in the c9, t11 CLA is separated from the mix by selective esterification with lauryl alcohol using *Geotrichum Candidum* as a catalyst. The enriched c9, t11 CLA is hydrolyzed and converted to the triglyceride. After the esterification step and separation the remaining CLA free acids are enriched in ti 0, c12 CLA.

Commercially CLA is available as Clarinol® A-80 and A-95 from Loders-Croklaan, Channahon, Ill. and Neobee® CLA 80 and 90 from Stepan, North Field, Ill.

Water-In-Oil Surfactant

A wide variety of silicone surfactants are useful herein. These silicones are typically organically modified organopolysiloxanes such as dimethicone copolyols.

Nonlimiting examples of dimethicone copolyols and other silicone surfactants useful herein include polydimethylsiloxane polyether copolymers with pendant polyethylene oxide side chains, polydimethylsiloxane polyether copolymers with pendant polypropylene oxide side chains, polydimethylsiloxane polyether copolymers with pendant mixed polyethylene oxide and polypropylene oxide side chains, polydimethylsiloxane polyether copolymers with pendant mixed poly(ethylene)(propylene)oxide side chains, polydimethylsiloxane polyether copolymers with pendant organobetaine side chains, polydimethylsiloxane polyether copolymers with pendant carboxylate side chains, polydimethylsiloxane polyether copolymers with pendant quaternary ammonium side chains; and also further modifications of the preceding copolymers containing pendant C2–C30 straight, branched, or cyclic alkyl moieties. Examples of commercially available dimethicone copolyols useful herein sold by Dow Corning Corporation are Dow Corning® 190, 193, Q2-5220, 2501 Wax, 2-5324 fluid, and 3225C (this latter material being sold as a mixture with cyclomethicone). Cetyl dimethicone copolyol is commercially available as a mixture with polyglyceryl-4 isostearate (and) hexyl laurate and is sold under the tradename ABIL® WE-09 (available from Goldschmidt). Cetyl dimethicone copolyol is also commercially available as a mixture with hexyl laurate (and) polyglyceryl-3 oleate sold under the tradename ABIL® WS-08 (also available from Goldschmidt). Other nonlimiting examples of dimethicone copolyols include lauryl dimethicone copolyol, dimethicone copolyol acetate, dimethicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, dimethicone copolyol sulfosuccinate and dimethicone copolyol stearate. Most preferred is PEG-10 Dimethicone available from Shin Etsu.

Amounts of the silicone surfactant may range from about 0.1 to about 30%, preferably from about 1 to about 10%, optimally from about 1.5 to about 5% by weight of the composition.

Organic Sunscreen Agent

Sunscreen agents of the present invention will have at least one chromophoric group absorbing within the ultraviolet ranging from 290 to 400 nm. Chromophoric organic sunscreen agents may be divided into the following categories (with specific examples) including: p-Aminobenzoic acid, its salts and its derivatives (ethyl, isobutyl, glyceryl esters; p-dimethylaminobenzoic acid); Anthranilates (o-aminobenzoates; methyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, alpha-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzone, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone; 4-Isopropyldibenzoylmethane; Butylmethoxydibenzoylmethane; Etocrylene; and 4-isopropyl-dibenzoylmethane).

Particularly useful are: 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl 4-[bis(hydroxypropyl)]aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfoniobenzoxazoic acid and mixtures thereof.

Suitable commercially available organic sunscreen agents are those identified under the following Table.

TABLE I

| CTFA NAME | TRADE NAME | SUPPLIER |
| --- | --- | --- |
| Benzophenone-3 | UVINUL M-40 | BASF Chemical Co. |
| Benzophenone-4 | UVINUL MS-40 | BASF Chemical Co. |
| Benzophenone-8 | SPECTRA-SORB UV-24 | American Cyanamid |
| DEA-Methoxycinnamate | BERNEL HYDRO | Bernel Chemical |
| Ethyl dihydroxypropyl-PABA | AMERSCREEN P | Amerchol Corp. |
| Glyceryl PABA | NIPA G.M.P.A. | Nipa Labs. |
| Homosalate | KEMESTER HMS | Humko Chemical |
| Menthyl anthranilate | SUNAROME UVA | Felton Worldwide |
| Octocrylene | UVINUL N-539 | BASF Chemical Co. |
| Octyl dimethyl PABA | AMERSCOL | Amerchol Corp. |
| Octyl methoxycinnamate | PARSOL MCX | Givaudan Corp. |
| Octyl salicylate | SUNAROME WMO | Felton Worldwide |
| PABA | PABA | National Starch |
| 2-Phenylbenzimidazole-5-sulphonic acid | EUSOLEX 232 | EM Industries |
| TEA salicylate | SUNAROME W | Felton Worldwide |
| 2-(4-Methylbenzylidene)-camphor | EUSOLEX 6300 | EM Industries |
| Benzophenone-1 | UVINUL 400 | BASF Chemical Co. |
| Benzophenone-2 | UVINUL D-50 | BASF Chemical Co. |
| Benzophenone-6 | UVINUL D-49 | BASF Chemical Co. |
| Benzophenone-12 | UVINUL 408 | BASE Chemical Co. |
| 4-Isopropyl dibenzoyl methane | EUSOLEX 8020 | EM Industries |
| Butyl methoxy dibenzoyl methane | PARSOL 1789 | Givaudan Corp. |
| Etocrylene | UVINUL N-35 | BASF Chemical Co. |

Most preferred are organic sunscreens in liquid form when at ambient (25° C.) temperature. Illustrative is octyl methyoxycinnamate.

Dispersed Aqueous Phase

The compositions of the present invention comprise from about 5% to about 90%, more preferably from about 30% to about 75%, and even more preferably from about 45% to about 60% of a dispersed aqueous phase. In emulsion technology, the term "dispersed phase" means that the phase exists as small particles or droplets suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore.

The aqueous phase can be water, or a combination of water and one or more water soluble or dispersible ingredients. Nonlimiting examples of such optional ingredients include thickeners, acids, bases, salts, chelants, gums, water-soluble or dispersible alcohols and polyols, buffers, preservatives, and colorants.

Optional Components

The composition of the present invention may contain a variety of other ingredients that are conventionally used in given product types provided that they do not unacceptably alter the benefits for the invention.

A component of the present invention may be a crosslinked silicone (organopolysiloxane) elastomer. No specific restriction exists as to the type of curable organopolysiloxane composition that can serve as starting material for the crosslinked silicone elastomer. Examples in this respect are addition reaction-curing organopolysiloxane compositions which cure under platinum metal catalysis by the addition reaction between SiH-containing diorganopolysiloxane and organopolysiloxane having silicon-bonded vinyl groups; condensation-curing organopolysiloxane compositions which cure in the presence of an organotin compound by a dehydrogenation reaction between hydroxyl terminated diorganopolysiloxane and SiH-containing diorganopolysiloxane; condensation-curing organopolysiloxane compositions which cure in the presence of an organotin compound or a titanate ester, by a condensation reaction between a hydroxyl terminated diorganopolysiloxane and a hydrolyzable organosilane (this condensation reaction is exemplified by dehydration, alcohol-liberating, oxime-liberating, amine-liberating, amide-liberating, carboxyl-liberating, and ketone-liberating reactions); peroxide-curing organopolysiloxane compositions which thermally cure in the presence of an organoperoxide catalyst; and organopolysiloxane compositions which are cured by high-energy radiation, such as by gamma-rays, ultraviolet radiation, or electron beams.

Addition reaction-curing organopolysiloxane compositions are preferred for their rapid curing rates and excellent uniformity of curing. A particularly preferred addition reaction-curing organopolysiloxane composition is prepared from:

(A) an organopolysiloxane having at least 2 lower alkenyl groups in each molecule;
(B) an organopolysiloxane having at least 2 silicon-bonded hydrogen atoms in each molecule; and
(C) a platinum-type catalyst.

The crosslinked siloxane elastomer may either be an emulsifying or non-emulsifying crosslinked organopolysiloxane elastomer or combinations thereof. The term "non-emulsifying," as used herein, defines crosslinked organopolysiloxane elastomer from which polyoxyalkylene units are absent. The term "emulsifying," as used herein, means crosslinked organopolysiloxane elastomer having at least one polyoxyalkylene (e.g., polyoxyethylene or polyoxypropylene) unit.

Particularly useful emulsifying elastomers are polyoxyalkylene-modified elastomers formed from divinyl compounds, particularly siloxane polymers with at least two free vinyl groups, reacting with Si—H linkages on a polysiloxane backbone. Preferably, the elastomers are dimethyl polysiloxanes crosslinked by Si—H sites on a molecularly spherical MQ resin.

Preferred silicone elastomers are organopolysiloxane compositions available under the INCI names of dimethicone/vinyl dimethicone crosspolymer, dimethicone crosspolymer and Polysilicone-11. Ordinarily these materials are provided as a 1–30% crosslinked silicone elastomer dissolved or suspended in a dimethicone fluid (usually cyclomethicone). For purposes of definition "crosslinked silicone elastomer" refers to the elastomer alone rather than the total commercial compositions which also include a solvent (eg dimethicone) carrier.

Dimethicone/vinyl dimethicone crosspolymers and dimethicone crosspolymers are available from a variety of suppliers including Dow Corning (9040, 9041, 9045, 9506 and 9509), General Electric (SFE 839), Shin Etsu (KSG-15, 16, 18 [dimethicone/phenyl vinyl dimethicone crosspolymer]), and Grant Industries (Gransil™ line of materials), and lauryl dimethicone/vinyl dimethicone crosspolymers supplied by Shin Etsu (e.g, KSG-31, KSG-32, KSG-41, KSG-42, KSG-43, and KSG-44).

Other suitable commercially available silicone elastomer powders include vinyl dimethicone/methicone silesquioxane crosspolymers from Shin Etsu sold as KSP-100, KSP-101, KSP-102, KSP-103, KSP-104, KSP-105, and hybrid silicone powders that contain a fluoroalkyl group or a phenyl group sold by Shin Etsu as respectively KSP-200 and KSP-300. Also of use is Dow Corning 5-7070, a silicone amino elastomer emulsion with INCI name of silicone quaternium-16/glycidoxy dimethicone crosspolymer (and) trideceth-12.

The crosslinked silicone elastomers may range in concentration from about 0.01 to about 30%, preferably from about 0.1 to about 10%, optimally from about 0.5 to about 2% by weight of the cosmetic composition. These weight values exclude any solvent such as cyclomethicone found in commercial "elastomer" silicones such as the Dow Corning products 9040 and 9045. For instance, the amount of crosslinked silicone elastomer in 9040 and 9045 is between 12 and 13% by weight.

Most preferred as the silicone elastomer is 9045 which has a D5 cyclomethicone swelled elastomer particle size (based on volume and calculated as spherical particles) which averages about 38 micron, and may range from about 25 to about 55 micron.

The compositions may include from about 1% to about 80%, by weight of the composition, of a suitable carrier for the crosslinked organopolysiloxane elastomer component described above. The carrier, when combined with the cross-linked organopolysiloxane elastomer particles serves to suspend and swell the elastomer particles to provide an elastic, gel-like network or matrix. The carrier for the crosslinked siloxane elastomer is liquid under ambient conditions, and preferably has a low viscosity to provide for improved spreading on the skin.

Concentrations of the carrier may range from about 5% to about 60%, more preferably from about 5% to about 40%, by weight of the composition.

These liquid carriers may be organic, silicone-containing or fluorine-containing, volatile or non-volatile, polar or non-polar, provided that the liquid carrier forms a solution or other homogeneous liquid or liquid dispersion with the selected cross-linked siloxane elastomer at the selected siloxane elastomer concentration at a temperature of from about 28° C. to about 250° C., preferably from about 28° C. to about 78° C. The term "non-polar" typically means that the material has a solubility parameter below about 6.5 $(cal/cm^3)^{0.5}$.

The non-polar, volatile oil tends to impart highly desirable aesthetic properties to the compositions of the present invention. Consequently, the non-polar, volatile oils are preferably utilized at a fairly high level. Non-polar, volatile oils particularly useful in the present invention are silicone oils; hydrocarbons; and mixtures thereof. Examples of preferred non-polar, volatile hydrocarbons include polydecanes such as isododecane and isodecane (e.g., Permethyl-99A which is available from Presperse Inc.) and the C7–C8 through C12–C15 isoparaffins (such as the Isopar Series available from Exxon Chemicals). Particularly preferred volatile silicone oils are cyclic volatile silicones wherein the repeating unit ranges from about 3 to about 5; and linear silicones wherein the repeating unit ranges from about 1 to about 7. Highly preferred examples of volatile silicone oils include cyclomethicones of varying viscosities, e.g., Dow Corning 200, Dow Corning 244, Dow Corning 245, Dow Corning 344, and Dow Corning 345, (commercially available from Dow Corning Corp.); SF-1204 and SF-1202 Silicone Fluids, GE 7207 and 7158 (commercially available from G.E. Silicones) and SWS-03314 (commercially available from SWS Silicones Corp).

Compositions of the present invention may also contain $C_1$–$C_{20}$ alpha- and beta-hydroxy carboxylic acids and salts thereof. The salts are preferably alkaline metal, ammonium and $C_1$–$C_{12}$ alkanolammonium salts and mixtures thereof. The term "alpha-hydroxycarboxylic acids" includes not only hydroxy acids but also alpha-ketoacids and related compounds of polymeric forms of hydroxyacid.

Alpha-hydroxyacids are organic carboxylic acids in which one hydroxyl group is attached to the alpha carbon adjacent the carboxy group. The generic structure is as follows:

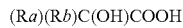

where Ra and Rb are H, F, Cl, Br, alkyl, aralkyl or aryl group of saturated or unsaturated, isomeric or non-isomeric, straight or branched chain or cyclic form, having 1 to 25 carbon atoms, and in addition Ra and Rb may carry OH, CHO, COOH and alkoxy groups having 1 to 9 carbon atoms. The alpha-hydroxyacids may be present as a free acid or in lactone form, or in a salt form with an organic base or an inorganic alkali. The alpha-hydroxyacids may exist as stereoisomers as D, L, and DL forms when Ra and Rb are not identical.

Typical alkyl, aralkyl and aryl groups for Ra and Rb include methyl, ethyl, propyl, isopropyl, butyl, pentyl, octyl, lauryl, stearyl, benzyl and phenyl. Most preferred among the alpha-hydroxyacids are glycolic acid, lactic acid, alpha-hydroxycaprylic acid, gluconolactone and combinations thereof.

Among the beta-hydroxycarboxylic acids, the most prominent and useful is salicylic acid.

Amounts of the hydroxy carboxylic acids may range from about 0.01 to about 15%, preferably from about 0.1 to about 12%, more preferably from about 1 to about 8%, optimally from about 2 to about 8% by weight of the total cosmetic composition.

Humectant may be incorporated into compositions of the present invention. Humectants are normally polyols. Representative polyols include glycerin, diglycerin, polyalkylene glycols and more preferably alkylene polyols and their derivatives including propylene glycol, dipropylene glycol, polypropylene glycol, polyethylene glycol and derivatives thereof, sorbitol, hydroxypropyl sorbitol, hexylene glycol, 1,2-butylene glycol, 1,2,6-hexanetriol, isoprene glycol, 2-methyl-1,3-propanediol, ethoxylated glycerol, propoxylated glycerol and mixtures thereof. Amounts of the humectant may range from about 0.01 to about 30%, preferably from about 0.1 to about 15%, optimally from about 2 to about 10% by weight of the composition.

Emollients may be formulated into the compositions. These emollients may be selected from hydrocarbons, silicones, fatty alcohols, fatty acids, synthetic or natural esters and combinations thereof. Amounts of the emollients may range from about 0.01 to about 30%, preferably from about 0.1 to about 10%, optimally from about 0.5 to about 5% by weight of the composition.

Hydrocarbons encompass mineral oil, polyalphaolefins and isoparaffins.

Among the ester emollients are:
(1) Alkenyl or alkyl esters of fatty acids having 10 to 20 carbon atoms. Examples thereof include isoarachidyl neopentanoate, isononyl isononanoate, oleyl myristate, oleyl stearate, octyl stearate and oleyl oleate.
(2) Ether-esters such as fatty acid esters of ethoxylated fatty alcohols.
(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
(4) Wax esters such as beeswax, spermaceti, myristyl myristate, stearyl stearate.
(5) Mono-, Di- and Triglyceride esters such as PEG-8 caprylic/capric triglyceride.
(6) Sterols esters, of which cholesterol fatty acid esters are examples thereof.

Most preferred is glycerol monostearate available from Kessco Corporation and Sterols sold under the trademark Generol 122®.

Natural esters which may be employed as emollients include olive oil, sunflower seed oil, safflower oil, cotton seed oil, rape seed oil, palm kernel oil, palm oil and mixtures thereof.

Fatty alcohols may also serve as emollients. These are typically formed from 10 to 30 carbon atoms and include cetyl, myristyl, palmityl, stearyl, isostearyl, hydroxystearyl, oleyl, linoleyl, behenyl alcohols and mixtures thereof.

Fatty acids having from 10 to 30 carbon atoms may also be included in the compositions of this invention. Illustrative of this category are pelargonic, lauric, myristic, palmitic, stearic, isostearic, hydroxystearic, oleic, linoleic, ricinoleic, arachidic, behenic and erucic acids. Amounts may range from about 0.1 to about 20%, preferably from about 1 to about 10%, optimally from about 2 to about 5% by weight.

The compositions of the present invention may comprise a skin lightening agent. When used, the compositions preferably comprise from about 0.1% to about 10%, more preferably from about 0.2% to about 5%, also preferably from about 0.5% to about 2%, by weight of the composition, of a skin lightening agent. Suitable skin lightening agents include niacinamide, kojic acid, arbutin, tranexamic acid, ethyl resorcinol, placental extract, ascorbic acid and derivatives thereof (e.g. magnesium ascorbyl phosphate, sodium ascorbyl phosphate, ascorbyl glucoside, and ascorbyl tetraisopalmitates). Other skin lightening materials suitable for use herein include Actiwhite® (Cognis), Emblica® (Rona), Azeloglicina (Sinerga) and extracts (e.g. mulberry extract).

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the composition. Most preferred is iodopropynyl butylcarbamate available from Lonza Corporation under the trademarks Glydant Plus and Glycasil L. Preservatives are preferably employed in amounts ranging from 0.001% to 2% by weight of the composition.

Compositions of the present invention may further include herbal extracts. Illustrative extracts include Centella Asiatica, Ginseng, Citrus Unshui, Ginko Biloba, Chamomile, Green Tea, Scullcap, Nettle Root, *Swertia Japonica*, Fennel and Aloe Vera extracts and combinations thereof. Amounts of each of the extracts on an actives basis may range from about 0.00001 to about 1%, preferably from about 0.001 to about 0.5%, optimally from about 0.005 to about 0.2% by weight of the composition.

Minor adjunct ingredients may also be present in the compositions. Among these may be vitamins such as Vitamin E esters, Vitamin C, Panthenol and any of the Vitamin B complexes (e.g. niacinamide and Vitamin B6). Retinoids may be employed including retinol, retinyl linoleate, retinyl acetate, retinoic acid and combinations thereof. Anti-irritant agents may also be present including those of steviosides, alpha-bisabolol and glycyhrizzinate salts. Each vitamin, retinoid or anti-irritant agent may be present in amounts ranging from about 0.0001 to about 1.0%, preferably from about 0.001 to about 0.5%, optimally from about 0.01 to about 0.3% by weight of the composition.

The cosmetic compositions can exhibit pH properties ranging from pH 2 to 10. A preferred embodiment has pH ranging from about 4.5 to about 7.0.

The compositions of the present invention can comprise one or more thickening agents, preferably from about 0.05% to about 10%, more preferably from about 0.1% to about 5%, and even more preferably from about 0.25% to about 4%, by weight for the composition. Nonlimiting classes of thickening agents include those selected from the group consisting of:

a. Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon—carbon double bonds and is derived from a polyhydric alcohol.

Examples of commercially available carboxylic acid polymers useful herein include the Carbomers, which are homopolymers of acrylic acid crosslinked with allyl ethers of sucrose or pentaerytritol. The Carbomers are available as the Carbopol® 900 series from Noveon Corporation (e.g. Carbopol® 954). In addition, other suitable carboxylic acid polymeric agents include copolymers of $C_{10-30}$ alkyl acrylates with one or more monomers of acrylic acid, methacrylic acid, or one of their short chain (i.e. $C_{1-4}$ alcohol) esters, wherein the crosslinking agent is an allyl ether of sucrose or pentaerytriotol. These copolymers are known as Acrylates/$C_{10-30}$ Alkyl Acrylate Crosspolymers and are commercially available as Carbopol® 1342, Carbopol® 1382, Ultrez® 21, Pemulen® TR-1, and Pemulen® TR-2, from Noveon Corporation.

b. Taurate Polymers

The compositions of the present invention can optionally comprise crosslinked taurate polymers useful as thickeners or gelling agents including anionic, cationic and nonionic polymers. Examples include Hydroxyethyl Acrylate/Sodium Acryloyidimethyl Taurate (e.g. Simulgel® NS and INS 100), Acrylate/Sodium Acryioyldimethyl Taurate (e.g. Simulgel® EG), Sodium Acryloyidimethyl Taurate (e.g. Simulgel® 800) and Ammonium Acryloyldimethyl Taurate/Vinyl Pyrrolidone (e.g. Aristoflex® AVC).

c. Polyacrylamide Polymers

The compositions of the present invention can optionally comprise polyacrylamide polymers, especially nonionic polyacrylamide polymers including substituted branched or unbranched polymers. Preferred among these polyacrylamide polymers is the nonionic polymer given the CTFA designation polyacrylamide and isoparaffin and laureth-7, available under the tradename Sepigel® 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

d. Polysaccharides

A wide variety of polysaccharides are useful herein. "Polysaccharides" refer to gelling agents that contain a backbone of repeating sugar (i.e., carbohydrate) units. Nonlimiting examples of polysaccharide gelling agents include those selected from the group consisting of cellulose, carboxymethyl hydroxyethylcellulose, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof.

e. Gums and Clays

Other thickening and gelling agents useful herein include materials that are primarily derived from natural sources. Nonlimiting examples include materials selected from the group consisting of acacia, aga, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, laponite, bentonite, hyaluronic acid, hydrated silica, hydroxypropyl chitosan, hydroxypropyl guar, karaya gum, kelp, locust bean gum, natto gum, potassium carrageenan, propylene glycol alginate, sclerotium gum, sodium carboxymethyl dextran, sodium carrageenan, tragacanth gum, xanthan gum, and mixtures thereof.

The compositions of the present invention may contain one or more particulate materials. Nonlimiting examples of particulate materials include colored and uncolored pigments, interference pigments, inorganic powders, organic powders, composite powders, optical brightener particles, and combinations thereof. Particulate materials may be present from about 0.01% to about 20%, more preferably from about 0.05% to about 10%, still more preferably from about 0.1% to about 5%, by weight of the composition.

Particulate materials useful herein include but are not limited to bismuth oxychloride, sericite, mica, mica treated with barium sulfate or titanium dioxide, zeolite, kaolin, silica, boron nitride, lauroyl lysine, nylon, talc, styrene, polystyrene, ethylene/acrylic acid copolymer, aluminum oxide, silicone resin, barium sulfate, calcium carbonate, cellulose acetate, PTFE, polymethyl methacrylate, starch, modified starches, silk, glass, and mixtures thereof. Preferred organic powders/fillers include polymeric particles chosen from the methylsilsesquioxane resin microspheres such as those sold by Toshiba Silicone under the name Tospearl 145A; microspheres of polymethylmethacrylates such as those sold by Seppic under the name Micropearl M 100; the spherical particles of crosslinked polydimethylsuloxanes, especially such as those sold by Dow Corning Toray Silicone under the name Trefil E 506C or Trefil E 505C; spherical particles of polyamide and more specifically Nylon 12, especially such as those sold by Atochem under the name Orgasol 2002N Nat C05; polystyrene microspheres such as those sold by Dyno Particles under the name Dynospheres; ethylene acrylate copolymer sold by Kobo under the name FloBead EA209; PTFE; polypropylene; aluminum starch octenylsuccinate such as sold by National Starch under the name Dry Flo; microspheres of polyethylene such as those sold by Equistar under the name of Microthene FN510-00; silicone resin; platelet shaped powder made from L-lauroyl lysine, and mixtures thereof. Especially preferred are spherical powders with an average primary particle size from 0.1 to 75 microns, preferably from 0.2 to 30 microns.

Also useful herein are interference pigments. Interference pigments, are defined as thin platelike layered particles having two or more layers of controlled thickness with different refractive indices that yield a characteristic reflected color from the interference of typically two, but occasionally more, light reflections, forming different layers of the platelike particle. The most common examples of interference pigments are micas layered with about 50–300 nm films of TiO2, Fe2O3, silica, tin oxide, and/or Cr2O3. Such pigments are often pearlescent. Useful interference pigments are available commercially from a wide variety of suppliers, for example, Rona (Timiron™ and Cichrona™), Presperse (Flonac™), Englehard (Duochrome™), Kobo (SK45-R and SK45-G), BASF (Sicopearls) and Eckart (e.g. Prestige Silk Red). Especially preferred are interference pigments with smaller particle sizes, with an average diameter of individual particles less than about 75 microns in the longest direction, preferably with an average diameter less than about 50 microns.

Other pigments useful in the present invention provide color primarily through selective absorption of specific wavelengths of visible light, and include inorganic pigments, organic pigments and combinations thereof. Examples of useful inorganic pigments include iron oxides, ferric ammonium ferrocyanide, manganese violet, ultramarine blue, and Chrome oxide. Organic pigments can include natural colorants and synthetic monomeric and polymeric colorants. An example is phthalocyanine blue and green pigment. Also useful are lakes, primary FD&C or D&C lakes and blends thereof. Also useful are encapsulated soluble or insoluble dyes and other colorants. Inorganic white or uncolored pigments useful in the present invention, for example TiO2, ZnO, or $ZrO_2$, are commercially available from a number of sources.

Preferred colored or uncolored non-interference-type pigments have a primary average particle size of from about 10 nm to about 100,000 nm, more preferably from about 20 nm to about 5,000 nm, even more preferably from about 20 nm to about 1000 nm. Mixtures of the same or different pigment/powder having different particle sizes are also useful herein (e.g., incorporating a TiO2 having a primary particle size of from about 100 nm to about 400 nm with a TiO2 having a primary particle size of from about 10 nm to about 50 nm).

The pigments/powders can be surface treated to provide added stability of color and/or for ease of formulation. Non-limiting examples of suitable coating materials include silicones, lecithin, amino acids, metal soaps, polyethylene and collagen. These surface treatments may be hydrophobic or hydrophilic, with hydrophobically treatments being preferred.

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

All documents referred to herein, including all patents, patent applications, and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

EXAMPLES I–V

A series of shine controlling facial skin creams is prepared by conventional methods for the following formulas with components listed as weight %.

| Component | I | II | III | IV | V |
|---|---|---|---|---|---|
| Phase A | | | | | |
| Deionized Water | Qs | Qs | Qs | Qs | Qs |
| Phase B (Surfactant Network) | | | | | |
| NET-WO (PEG-10 Dimethicone & Disteardimonium Hectorite & Cyclopentasiloxane | 1.8000 | 1.8000 | 1.8000 | 1.8000 | 1.8000 |
| KR 6017 (PEG-10 Dimethicone) | 1.6000 | 1.6000 | 1.8000 | 1.8000 | 1.8000 |
| Phase C (Humectant/Emollient) | | | | | |
| Glycerin | 10.0000 | 12.0000 | 12.0000 | 14.0000 | 9.0000 |
| Caprylic/Capric Triglycerides | 3.0000 | 3.0000 | 3.0000 | 3.0000 | 3.0000 |
| Phase D (Sunscreen) | | | | | |
| Parsol MCX (Ethylhexyl Methoxycinnamate) | 6.0000 | 6.0000 | 6.0000 | 6.0000 | 6.0000 |

-continued

| Component | I | II | III | IV | V |
|---|---|---|---|---|---|
| Phase E (Silicone) | | | | | |
| DC 9045 (Dimethicone Crosspolymer and Cyclopentasiloxane) | 26.0000 | 26.0000 | 26.0000 | 26.0000 | 26.0000 |
| Phase F (Visual Enhancement) | | | | | |
| Z-COTE HP1 (Zinc Oxide and Triethoxycaprylsilane) | 2.0000 | 2.0000 | 2.0000 | 2.0000 | 2.0000 |
| Phase G | | | | | |
| Clarinol ® A-80 (Conjugated Linoleic Acid) | 0.500 | 0.500 | 1.0000 | 1.0000 | 1.3000 |
| Herbal Extracts/Nutrients* | 1.9000 | 1.9000 | 1.9000 | 1.9000 | 1.9000 |
| Phase H (Fragrance/Anti-Oxidant/Preservative) | | | | | |
| Fragrance | 0.3500 | 0.3500 | 0.3500 | 0.3500 | 0.3500 |
| Disodium EDTA | 0.0500 | 0.0500 | 0.0500 | 0.0500 | 0.0500 |
| Glydant Plus Liquid (DMDM Hydantoin and Iodopropynyl Butylcarbamate) | 0.2000 | 0.2000 | 0.2000 | 0.2000 | 0.2000 |

*Includes: Vitamin E Acetate, Vitamin A Palmitate, SK-Influx (Cosmoferm), Bisabolol, Borage Oil, Coriander Seed Oil, Sodium Lactate, Sodium Ascorbyl Phosphate, Betula Alba Extract (White Birch), DL-Panthenol, Sodium PCA (50%), Hydrolyzed Milk Protein, Pomegranate Extract, Cholesterol and Stearic Acid.

The skin creams in the above Examples can be formulated in the following manner. A ten liter vessel is charged with the water of Phase A and the components of Phase B. The mixed phases are stirred at 40° C. Thereinto with stirring are added the components from Phase C, D, E and F. Stirring at 40° C. is then continued for another hour subsequent to the addition of the last component. The resultant mixture is then cooled to 30° C. and each of Phase G and then H are added under slow agitation of the batch.

EXAMPLE VI

A study on gloss was conducted. The method employed for the study was as follows.

Method for In-Vitro Optical Properties Measurement

Intrinsic optical properties of the formulas as films were measured using a Hunter Lab—Lab Scan XE (Hunter Associates Laboratory, Inc. Reston, Va.) and Statistical Glossmeter-Novo Gloss (Paul N. Gardner Company, Inc. Pompano Beach, Fla.) on Leneta black and white draw-down card form 2A-Opacity (The Leneta Company, Mahwah, N.J.). A 3 ml film casting applicator (Paul N. Gardner Company, Inc. Pompano Beach, Fla.) was used to cast about 75, product films on the draw-down cards. First, about 3–5 grams of the test formula was filled into the gap of the applicator on the draw-down card. The applicator was held and moved over products smoothly to get uniform product films. These films were dried in an air-conditioned room (temperature circa 22° C.) for 12 hours. By following the measurement procedure specified in the instrument menu and commercially supplied computer software, opacity (hiding power) and colors (a*, b* and L*) were measured using Lab Scan XE. Gloss data of the films were measured using Novo Gloss at 60 degree. The opacity data in percentage value is the measurement of hiding power of the test film needed to cover the black background on the draw-down card. Complete opacity (100%) means that no black background can be seen through the test film. The color measurement is presented by Hunter lab color space a*, b* and L*. Term a* is green-red space. Term b* is blue-yellow space and L* is black-white space. For example, a larger L* value means more white, and smaller b* value means more blue. Gloss is reported as g-u (Gloss unit). This unit relates to light intensity reflected from the surface of the test film. A higher value of gloss means a more shining film.

Opacity is measured by the percentage ratio of product film whiteness on the black background (L*B) to whiteness on the white background (L*W). Thus, the value "y" is a measure of opacity on the whiteness axis.

Compositions used in the study were formulated as reported in the Table below.

| Water-In-Oil Base Formula | |
|---|---|
| Component | Weight % |
| Water | 47.47 |
| Elastomer (DC 9045 Silicone Gel) | 26.00 |
| Glycerin | 10.00 |
| Parsol MCX ® (EthylhexylMethoxyCinnamate) | 6.00 |
| Caprylic/Capric Triglycerides | 3.00 |
| Zinc Oxide Powder | 2.00 |
| Herbal Extracts/Nutrients* | 2.08 |
| NET-WO (PEG-10 Dimethicone & Disteardimonium Hectorite & Cyclopentasiloxane) | 1.80 |
| Timiron ® MP-111 | 0.50 |
| PEG-10 Dimethicone | 0.60 |
| Fragrance | 0.30 |
| Glydant Plus Liquid ® | 0.20 |
| Disodium EDTA | 0.05 |

*See Example I for identity of Herbal Extracts/Nutrients (excludes Clarinol ® A-80).

The base formula is a water-in-oil emulsion into which four different concentrations of CLA (Clarinol A-80®) were formulated. The CLA included 37% of c9, t11 and 38% of t10, c12 isomers. The base formula was reduced in water content equivalent to the amount of CLA added to maintain 100% by weight. The Table below reports the CLA levels in the four compositions and their gloss and Opacity values. The values reveal a very significant decrease in gloss upon addition of 1% CLA. Compare composition A (control) to composition B. A further decrease is achieved with compositions C and D having 2% and 3% CLA, respectively. Organic sunscreens substantially increase gloss. This adverse effect is seen in comparison of composition A to AA.

| Composition | Conjugated Linoleic Acid (Weight %) | Gloss (g-u) | Opacity (Y) |
|---|---|---|---|
| A | 0.00 | 28.5 | 5.24 |
| AA* | 0.00 | 12.1 | 5.68 |
| B | 1.00 | 8.9 | 7.72 |
| C | 2.00 | 4.6 | 8.48 |
| D | 3.00 | 3.5 | 9.71 |

**Base Formula without Parsol MCX ® (sunscreen)

The effect of CLA on an oil-in-water emulsion was also evaluated. The O/w emulsion has a base formula shown in the Table below. Four concentrations of CLA (Clarinol A-80®) were formulated into the base. Water content was reduced in each formula according to the amount of CLA present to maintain 100% by weight.

| Oil-In-Water Base Formula | |
|---|---|
| Component | Weight % |
| Water | 54.00 |
| Elastomer (DC 9045 Silicone Gel) | 20.00 |
| Glycerin | 9.00 |
| Parsol MCX ® (EthylhexylMethoxyCinnamate) | 6.00 |
| Zinc Oxide Powder | 2.10 |
| Polysorbate 40 | 1.62 |
| Cetyl Alcohol | 1.55 |
| Silicone Fluid 200/50 cts | 1.00 |
| Timiron ® MP-111 | 1.00 |
| Aristoflex AVC ® | 0.80 |
| Glycerol Monostearate | 0.78 |
| DC 5225C | 0.50 |
| Ganspearl ® GMP 0820 (PMMA) | 0.50 |
| Phenoxyethanol | 0.40 |
| Fragrance | 0.30 |
| Methylparaben | 0.20 |
| Glycacil ® L | 0.10 |
| Propylparaben | 0.10 |
| Disodium EDTA | 0.05 |

Results are recorded in the following Table. Values reveal a significant reduction in gloss upon addition of 1% CLA. This effect levels off at 3%.

| Composition | Conjugated Linoleic Acid (Weight %) | Gloss (g-u) | Opacity (Y) |
|---|---|---|---|
| A | 0.00 | 9.7 | 11.82 |
| AA* | 0.00 | 7.8 | 11.08 |
| B | 1.00 | 4.1 | 10.57 |
| C | 2.00 | 2.6 | 10.13 |
| D | 3.00 | 2.2 | 10.33 |

*Base Formula without Parsol MCX ® (sunscreen).

Opacity increased with addition of CLA to the W/O base formula. In the O/W base formula opacity decreased slightly with an increase of CLA presence. Effects on improved opacity and gloss reduction therefore are seen to be more significant with W/O emulsions compared to O/W type.

What is claimed is:

1. A cosmetic composition which is a water-in-oil emulsion comprising:
    (i) from about 0.1 to about 30% by weight of a water-in-oil emulsifying silicone surfactant;
    (ii) from about 0.1 to about 30% by weight of an organic sunscreen agent; and
    (iii) from about 0.1 to about 3% of a conjugated linoleic acid.

2. The composition according to claim 1 wherein the water-in-oil surfactant is a silicone copolyol.

3. The composition according to claim 1 wherein the conjugated linoleic acid is present in an amount from about 0.5 to about 2% by weight of the composition.

4. The composition according to claim 1 wherein the conjugated linoleic acid consists essentially of at least 30% by weight of total conjugated linoleic acid present in the composition of a mixture of cis-9, trans-11 and trans-10, cis-12 linoleic acids.

5. The composition according to claim 4 wherein the conjugated linoleic acid consists essentially of at least 40% by weight of total conjugated linoleic acid present in the composition of a mixture of cis-9, trans-11 and trans-10, cis-12 linoleic acids.

6. The composition according to claim 1 further comprising from about 0.01 to about 30% by weight of a crosslinked silicone elastomer.

7. The composition according to claim 6 wherein the silicone elastomer is formed from siloxane polymers with at least two free vinyl groups reacting with Si—H linkages on a polysiloxane backbone.

8. The composition according to claim 6 wherein the silicone elastomer is selected from the group consisting of dimethicone/vinyl dimethicone crosspolymer, dimethicone crosspolymer and polysilicone-11.

9. The composition according to claim 1 wherein the sunscreen is ethylhexylmethoxycinnamate.

* * * * *